(12) United States Patent
Mccrayer (10) Patent No.: US 12,186,230 B1
(45) Date of Patent: Jan. 7, 2025

(54) URINATION ASSISTANCE APPARATUS

(71) Applicant: Deborah Ann Mccrayer, Brooklyn, MD (US)

(72) Inventor: Deborah Ann Mccrayer, Brooklyn, MD (US)

( * ) Notice: Subject to any disclaimer, the term of this patent is extended or adjusted under 35 U.S.C. 154(b) by 0 days.

(21) Appl. No.: 18/777,009

(22) Filed: Jul. 18, 2024

Related U.S. Application Data (63) Continuation-in-part of application No. 29/950,629, filed on Jul. 3, 2024.

(51) Int. Cl.
*A61F 5/453* (2006.01)

(52) U.S. Cl.
CPC .................................. *A61F 5/453* (2013.01)

(58) Field of Classification Search
CPC ............ A61F 5/453; A47K 11/12; E03D 9/00
USPC ......................................................... 4/144.1
See application file for complete search history.

(56) References Cited

U.S. PATENT DOCUMENTS

| | | | | |
|---|---|---|---|---|
| 105,979 | A * | 8/1870 | Price | |
| 2,522,273 | A * | 9/1950 | Johnson | A61G 9/006 |
| | | | | 4/144.1 |
| 2,664,573 | A * | 1/1954 | Taylor | A61F 5/445 |
| | | | | 4/661 |
| 5,285,532 | A * | 2/1994 | Sealy | A47K 11/12 |
| | | | | 4/144.1 |
| 6,327,716 | B1 | 12/2001 | Kaus | |
| 7,325,256 | B1 | 2/2008 | Pecinka, Sr. | |
| 9,301,870 | B2 | 4/2016 | Shelton | |
| D763,440 | S | 8/2016 | Garzon et al. | |
| 9,492,308 | B2 | 11/2016 | Plath | |
| 10,865,555 | B2 * | 12/2020 | Abrahams | B67C 11/02 |
| D935,014 | S | 11/2021 | Könings | |
| 11,639,244 | B2 | 5/2023 | Foda et al. | |
| 2006/0064034 | A1 | 3/2006 | Stewart et al. | |
| 2007/0044213 | A1 | 3/2007 | Hall | |
| 2019/0388265 | A1 | 12/2019 | Gabrielson | |

FOREIGN PATENT DOCUMENTS

WO 2013147529 A1 10/2013

* cited by examiner

*Primary Examiner* — Huyen D Le (57) ABSTRACT

A urination assistance apparatus includes a base, a tube having an upper end and a lower end, a joint assembly, and a urine funnel. The tube is attached to the base at the lower end and attached to the joint assembly at the upper end. The joint assembly connects the urine funnel to the tube.

8 Claims, 7 Drawing Sheets

URINATION ASSISTANCE APPARATUS

FIELD OF THE INVENTION

The present invention relates generally to urination assistance apparatuses. More specifically, the present invention is a standalone urination assistance apparatus that is designed for male use. However, the present invention is not limited to this option, and it may further be adapted for different purposes.

BACKGROUND OF THE INVENTION

In various circumstances, people may have limited or impaired mobility such that typical urination processes are challenging or impossible. For example, some people may experience or have a disability that impairs mobility. Moreover, when males use typical bowl toilets to urinate in a standing position, there is usually some splashing of urine as the urine falls into the toilet bowl. This is especially the case for a physically disabled person.

Therefore, it is an objective of the present invention to provide a urination assistance apparatus that overcomes the problems set forth above.

SUMMARY OF THE INVENTION

The present invention discloses a urination assistance apparatus. It comprises a base, a tube having an upper end and a lower end, a joint assembly, and a urine funnel. The tube is attached to the base at the lower end and attached to the joint assembly at the upper end. The joint assembly connects the urine funnel to the tube.

In one embodiment, the tube comprises a telescopic tube.

In one embodiment, the telescopic tube comprises a height adjustment mechanism to change the height of the telescopic tube.

In one embodiment, the telescopic tube comprises a first tube section and a second tube section, the first tube section being received in the second tube section.

In one embodiment, the height adjustment mechanism is located at an upper end of the second tube section and configured to allow the first tube section to slide in the second tube section and lock the position of the first tube section once a desired height is achieved.

In one embodiment, the first tube section comprises a first alignment groove, and the second tube section a corresponding second alignment groove.

In one embodiment, the height adjustment mechanism comprises a tube connector and a knob. The knob is configured to when tightened engage the first alignment groove of the first tube section to lock the first tube section, and when loosened allow the first tube section to slide in the second tube section.

In one embodiment, the joint assembly comprises a vertical rotating member to allow the urine funnel to rotate vertically.

In one embodiment, the joint assembly further comprises a horizontal rotating member to allow the urine funnel to rotate horizontally.

In one embodiment, the joint assembly further comprises a funnel attachment member allowing the urine funnel to be attached to the joint assembly.

In one embodiment, the funnel attachment member comprises a funnel attachment hole.

In one embodiment, the urine funnel comprises a flared first end and a second end, wherein the flared first end comprises a tapering receptacle for receiving urine, and the second end comprises a discharging opening.

In one embodiment, the urine funnel comprises an attachment rod that is configured to be inserted and fixed in the funnel attachment hole.

In one embodiment, the funnel attachment member further comprises a funnel adapter that is located between the attachment rod and an inner wall of the funnel attachment hole.

In one embodiment, the urine funnel comprises a splash guard around the first end of the urine funnel.

BRIEF DESCRIPTION OF THE DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the present invention. That is, the dimensions of the components of the present invention, independently and in relation to each other can be different. It should be noted that the drawings are schematic and not necessarily drawn to scale. Some drawings are enlarged or reduced to improve drawing legibility.

DETAIL DESCRIPTIONS OF THE INVENTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and is made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. When not explicitly defined herein, to the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subject matter disclosed under the header.

Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise indicated, the drawings are intended to be read together with the specification and are to be considered a portion of the entire written description of this invention. As used in the following description, the terms "horizontal", "vertical", "left", "right", "up", "down" and the like, as well as adjectival and adverbial derivatives thereof (e.g., "horizontally", "rightwardly", "upwardly", "radially", etc.), simply refer to the orientation of the illustrated structure as the particular drawing figure faces the reader. Similarly, the terms "inwardly," "outwardly" and "radially" generally refer to the orientation of a surface relative to its axis of elongation, or axis of rotation, as appropriate. As used herein, the term "proximate" refers to positions that are situated close/near in relationship to a structure. As used in the following description, the term "distal" refers to positions that are situated away from positions.

The present disclosure includes many aspects and features. Moreover, while many aspects and features relate to, and are described in the context of urination assistance apparatuses, embodiments of the present disclosure are not limited to use only in this context.

The present invention is a urination assistance apparatus that is specifically designed to assist in urination especially when a male user urinates in a standing position.

Referring now to the figures of the present disclosure. The urination assistance apparatus of the present invention comprises a base 100, a tube 200 having an upper end 201 and a lower end 202, a joint assembly 300, and a urine funnel 400.

The base 100 is configured to support the components of the present invention. It should be noted that the base 100 can be of any shape, size, material, features, type or kind, orientation, location, quantity, components, and arrangements of components that would allow the present invention to fulfill the objectives and intents of the present invention. In a preferred embodiment, the base 100 has a round shape. However, it is contemplated that other shapes are also possible, including but not limited to triangle, square, rectangle, pentagon, hexagon, rhombus, oval, diamond, star, irregular polygon, etc. In one embodiment, the base 100 may be sized and weighted to provide stability to the apparatus of the present invention. In a preferred embodiment, the base 100 may be provided with casters, preferably locking casters, such that the apparatus of the present invention can be moved with ease.

The tube 200 is connected between the funnel 400 and base 100. It should be noted that the tube 200 can be of any shape, size, material, features, type or kind, orientation, location, quantity, components, and arrangements of components that would allow the present invention to fulfill the objectives and intents of the present invention. In a preferred embodiment, the base 100 has a round shape. In the illustrated embodiment, the tube 200 is an elongated tube. The tube 200 is attached to the base at the lower end 202 and attached to the joint assembly 300 at the upper end 201.

Figure 7:
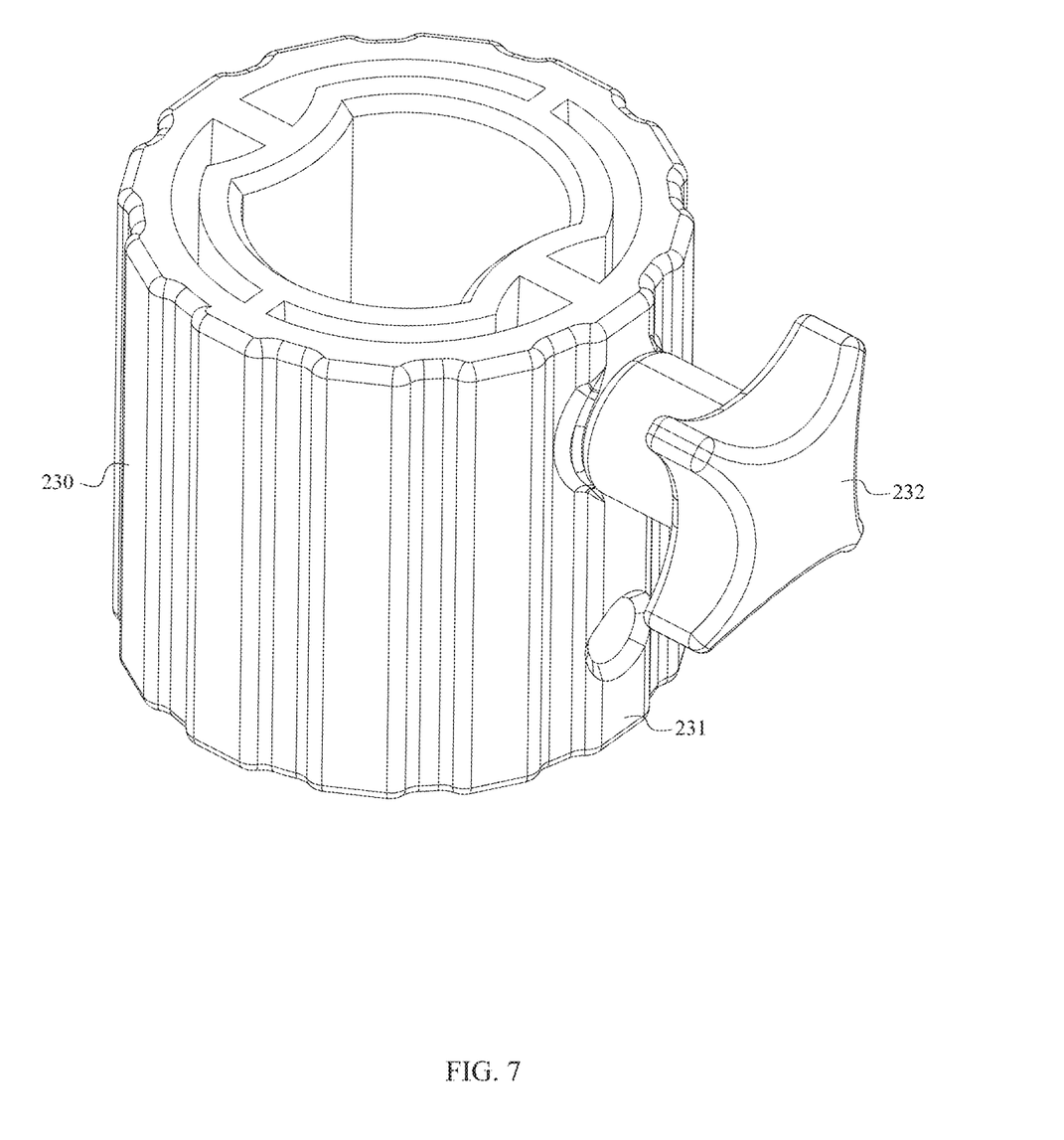
FIG. 7 depicts a perspective view of the height adjustment mechanism of the present invention.

In a preferred embodiment, the tube 200 comprises a telescopic tube. The telescopic tube allows the user to adjust the height of the urine funnel 400 in use. In a preferred embodiment, the telescopic tube comprises a height adjustment mechanism 230 to change the height of the telescopic tube. The height adjustment mechanism 230 can be any suitable mechanism that is capable of changing the length of the telescopic tube. Preferably, the telescopic tube comprises a first tube section 210 and a second tube section 211. The first tube section 210 is received in the second tube section 211. Typically, the first tube section 210 is greater than the second tube section 211 in length. For example, the first tube section 210 may have a length of 12 inches, while the second tube section 211 may have a length of 18 inches. In one embodiment, the height adjustment mechanism 230 is located at an upper end of the second tube section 220 and configured to allow the first tube section 210 to slide in the second tube section 220 and lock the position of the first tube section 210 once a desired height is achieved. In another preferred embodiment, the first tube section 210 comprises a first alignment groove 211, and the second tube section 220 comprises a corresponding second alignment groove 221. The first alignment groove 211 and the second alignment groove 221 can facilitate the alignment of the first tube section 210 with the second tube section 220. In this embodiment, the height adjustment mechanism 230 may comprise a tube connector 231 and a knob 232. The knob 232 is configured to when tightened engage the first alignment groove 211 of the first tube section 210 to lock the first tube section 210 in position, and when loosened allow the first tube section 210 to slide in the second tube section 220. In another example, the first tube section 210 may comprise a plurality of adjustment holes along the first alignment groove 211, while the height adjustment mechanism 230 comprises a spring pin to allow height adjustment.

Figure 1:
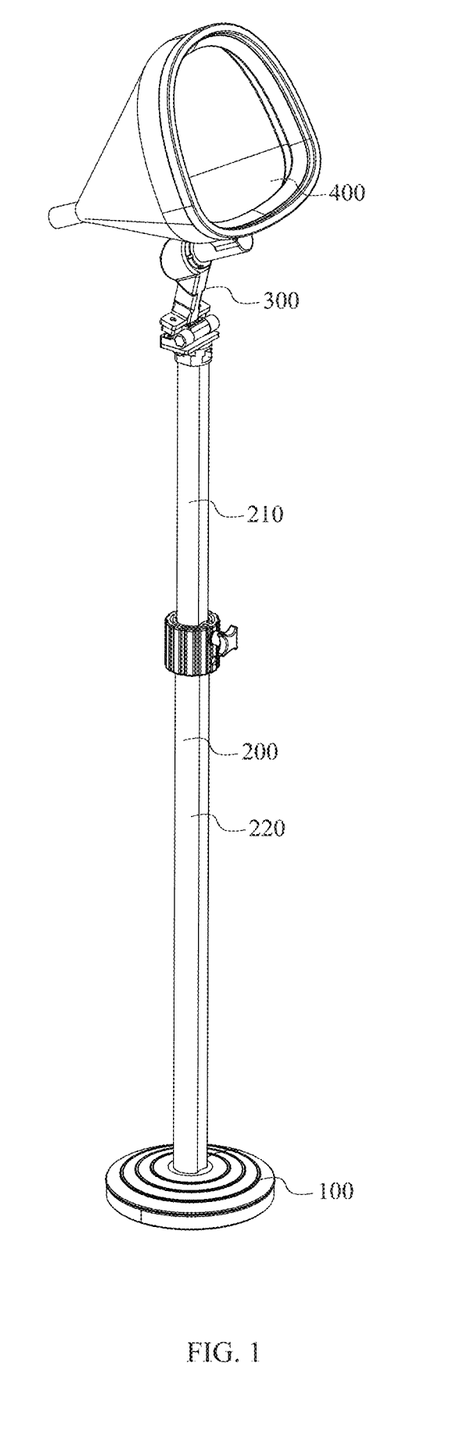
FIG. 1 depicts a top perspective view of the present invention.
Figure 2:
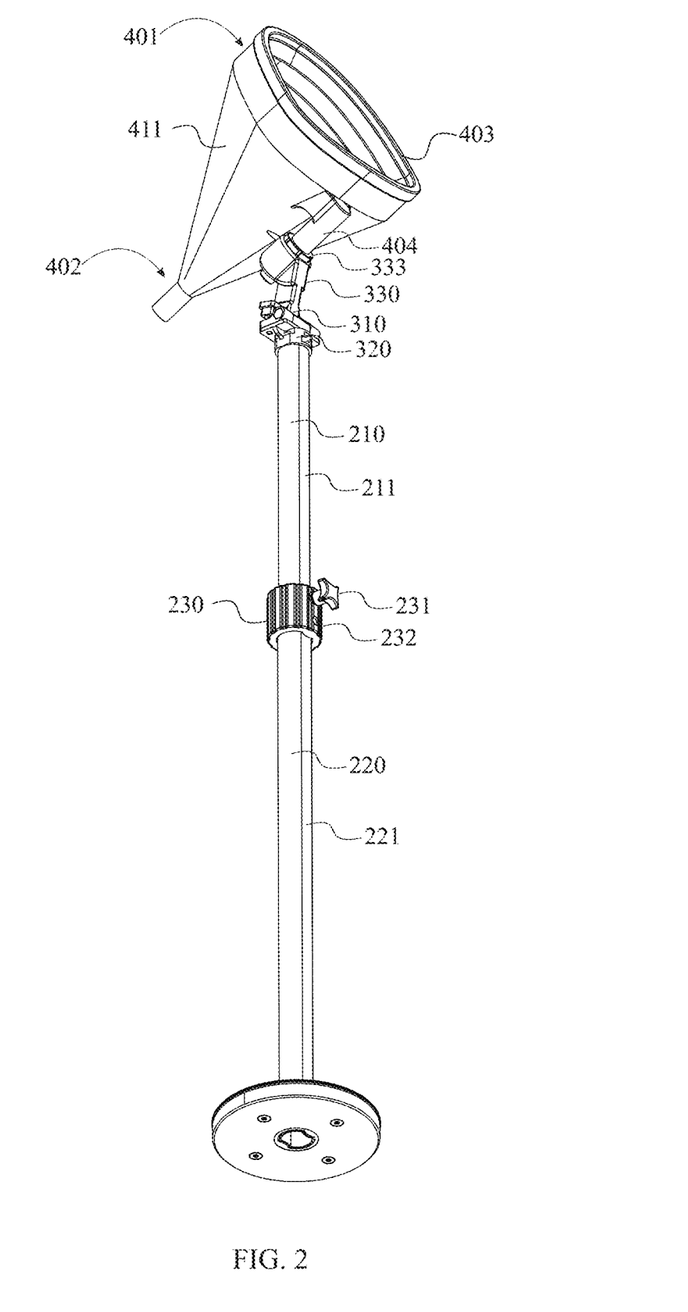
FIG. 2 depicts a bottom perspective view of the present invention.
Figure 3:
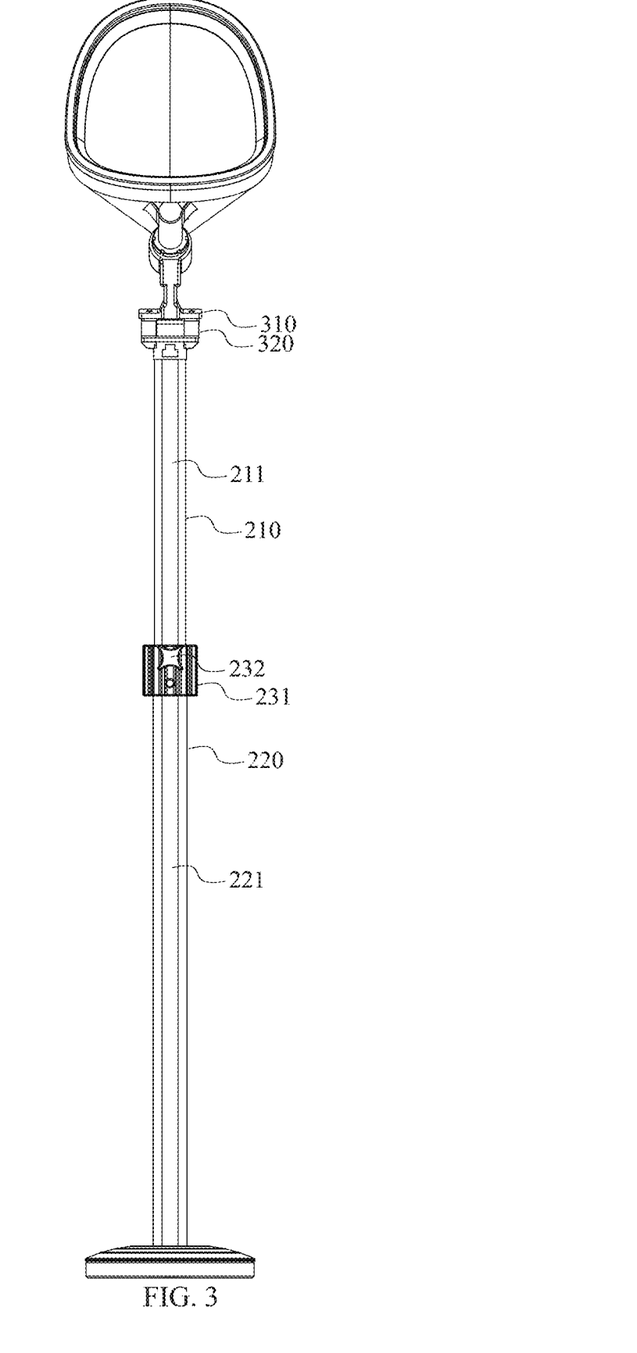
FIG. 3 depicts a front view of the present invention.
Figure 4:
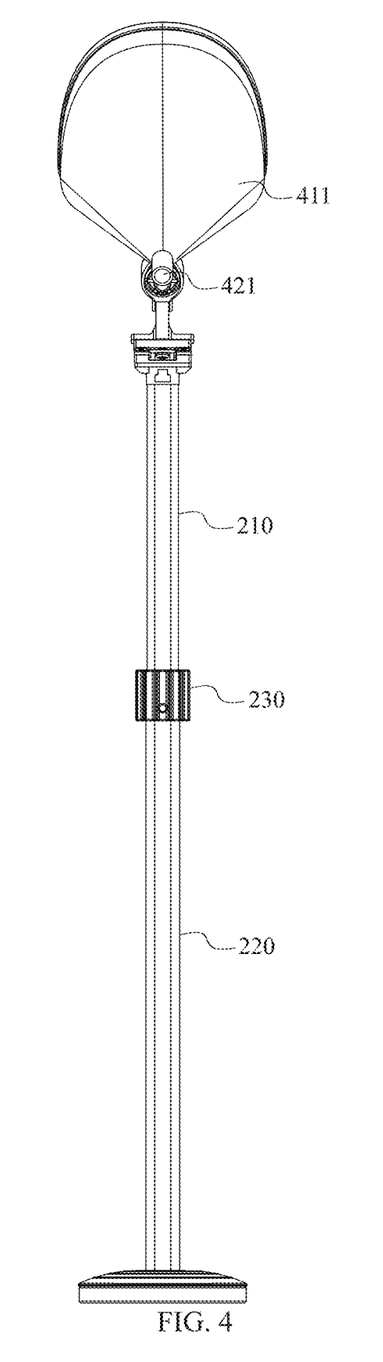
FIG. 4 depicts a rear view of the present invention.
Figure 5:
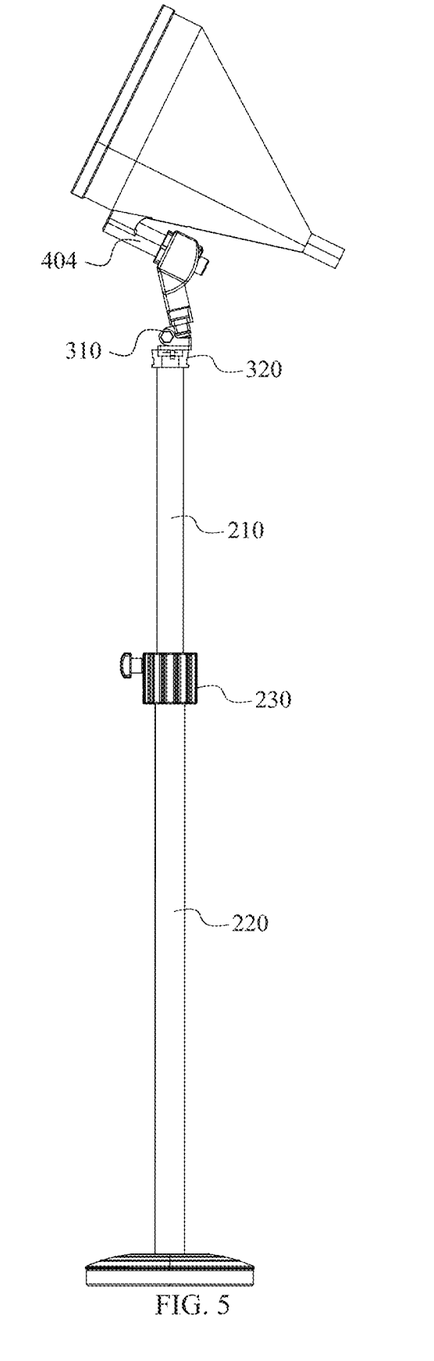
FIG. 5 depicts a right-side view of the present invention.
Figure 6:
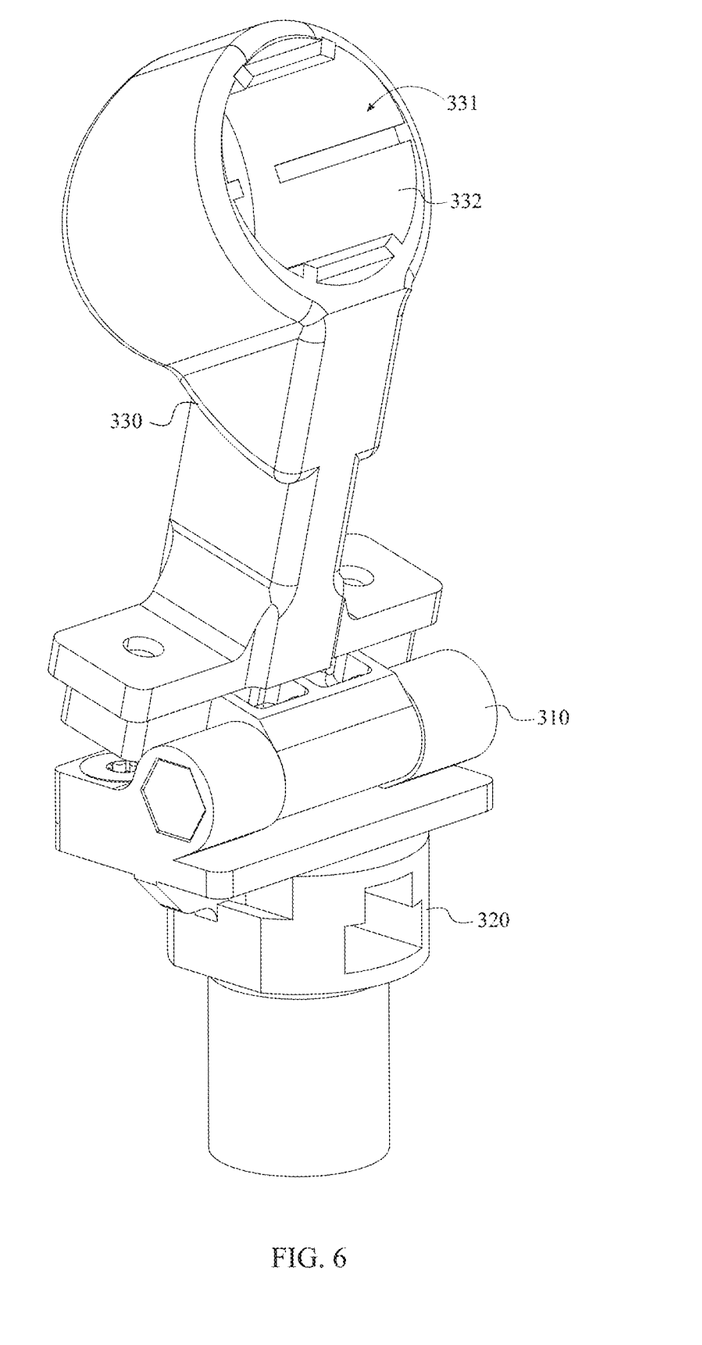
FIG. 6 depicts a perspective view of the joint assembly of the present invention.

The joint assembly 300 is configured to connect the urine funnel 400 to the tube 200. It should be noted that the joint assembly 300 can be of any shape, size, material, features, type or kind, orientation, location, quantity, components, and arrangements of components that would allow the present invention to fulfill the objectives and intents of the present invention. In a preferred embodiment, the joint assembly 300 comprises a vertical rotating member 310 to allow the urine funnel 400 to rotate vertically. In this embodiment, the urine funnel 400 may be tilted up/down. In another preferred embodiment, the joint assembly 300 further comprises a horizontal rotating member 320 to allow the urine funnel 400 to rotate horizontally such that the urine funnel 400 may turn to the right/left. Therefore, the urine funnel 400 may be adjusted to any desired angle. In this embodiment, the horizontal rotating member 320 may be located at the bottom of the joint assembly 300, and the first tube section 210 may be hollow at its top such that the horizontal rotating member 320 may be inserted into and rotated within the hollow top of the first tube section 210.

In one embodiment, the joint assembly 300 further comprises a funnel attachment member 330 allowing the urine funnel 400 to be attached to the joint assembly 300. Preferably, the funnel attachment member 330 comprises a funnel attachment hole 331 having an inner wall 332.

The urine funnel 400 comprises a flared first end 401 and a second end 402. The flared first end 401 comprises a tapering receptacle 411 for receiving urine, and the second end 402 comprises a discharging opening 421 to discharge urine collected within the tapering receptacle 411 into the toilet. When the urine stream is not directed directly at the discharging opening 421, the urine hits the walls of the receptacle 411 and runs down it to the discharging opening 421. In one embodiment, a flexible hose may be attached to the discharging opening 421 to direct the urine from the urine funnel 400 to the toilet. In one embodiment, the urine funnel 400 comprises a splash guard 403 around the first end 401 to help prevent urine from splashing and spilling around the toilet. It should be noted that the urine funnel 400 can be of any appropriate shape or configuration including, but not limited to, circular, oval, elliptical, rectangular or polygonal.

In one embodiment, the urine funnel 400 comprises an attachment rod 404 that is configured to be inserted and fixed in the funnel attachment hole 331. In this embodiment, the funnel attachment member 330 may further comprise a funnel adapter 33 that is located between the attachment rod 404 and the inner wall 332 of the funnel attachment hole 331.

It is envisioned that the sizes of the components forming the present invention such as the base 100, the tube 200, the joint assembly 300, and the urine funnel 400 can vary based on design requirements.

Although the disclosure has been explained in relation to its preferred embodiment, it is to be understood that many other possible modifications and variations can be made without departing from the spirit and scope of the disclosure.

What is claimed is:

1. A urination assistance apparatus comprising:
    a base;
    a tube having an upper end and a lower end;
    a joint assembly;
    a urine funnel;
    the tube being attached to the base at the lower end and being attached to the joint assembly at the upper end;
    the joint assembly connecting the urine funnel to the tube;
    wherein the tube comprises a telescopic tube;
    wherein the telescopic tube comprises a height adjustment mechanism to change the height of the telescopic tube;
    wherein the telescopic tube comprises a first tube section and a second tube section, the first tube section being received in the second tube section;
    wherein the height adjustment mechanism is located at an upper end of the second tube section and configured to allow the first tube section to slide in the second tube section and lock the position of the first tube section once a desired height is achieved; and
    wherein the first tube section comprises a first alignment groove, and the second tube section a corresponding second alignment groove.

2. The urination assistance apparatus as claimed in claim 1, wherein the height adjustment mechanism comprises a tube connector and a knob, the knob being configured to when tightened engage the first alignment groove of the first tube section to lock the first tube section, and when loosened allow the first tube section to slide in the second tube section.

3. A urination assistance apparatus comprising:
    a base;
    a tube having an upper end and a lower end;
    a joint assembly;
    a urine funnel;
    the tube being attached to the base at the lower end and being attached to the joint assembly at the upper end;
    the joint assembly connecting the urine funnel to the tube;
    wherein the joint assembly comprises a vertical rotating member to allow the urine funnel to rotate vertically;
    wherein the joint assembly further comprises a horizontal rotating member to allow the urine funnel to rotate horizontally; and
    wherein the joint assembly further comprises a funnel attachment member allowing the urine funnel to be attached to the joint assembly.

4. The urination assistance apparatus as claimed in claim 3, wherein the funnel attachment member comprises a funnel attachment hole.

5. The urination assistance apparatus as claimed in claim 4, wherein the urine funnel comprises a flared first end and a second end, wherein the flared first end comprises a tapering receptacle for receiving urine, and the second end comprises a discharging opening.

6. The urination assistance apparatus as claimed in claim 5, wherein the urine funnel comprises an attachment rod that is configured to be inserted and fixed in the funnel attachment hole.

7. The urination assistance apparatus as claimed in claim 6, wherein the funnel attachment member further comprises a funnel adapter that is located between the attachment rod and an inner wall of the funnel attachment hole.

8. The urination assistance apparatus as claimed in claim 5, wherein the urine funnel comprises a splash guard around the first end of the urine funnel.

* * * * *